United States Patent [19]
Grisar

[11] 4,221,808
[45] Sep. 9, 1980

[54] NOVEL ANTIHYPERTENSIVE AGENT

[75] Inventor: J. Martin Grisar, Cincinnati, Ohio

[73] Assignee: Richardson-Merrell Inc., Wilton, Conn.

[21] Appl. No.: 36,256

[22] Filed: May 4, 1979

[51] Int. Cl.$^2$ ............... A61K 31/335; C07D 317/06; C07D 317/44
[52] U.S. Cl. .................. 424/278; 260/340.5 R
[58] Field of Search ............... 424/278, 232; 260/340.5

[56] References Cited

U.S. PATENT DOCUMENTS

| | | | |
|---|---|---|---|
| 3,883,560 | 5/1975 | Suh et al. | 424/232 |
| 4,000,193 | 12/1976 | Lunts et al. | 260/559 S |

Primary Examiner—Stanley J. Friedman
Attorney, Agent, or Firm—L. Ruth Hattan; Eugene O. Retter; George W. Rauchfuss, Jr.

[57] ABSTRACT

This invention is to the compound 5-[2-[[3-(1,3-benzodioxol-5-yl)-1-methylpropyl]amino]-1-hydroxyethyl]-2-methoxybenzamide having the formula,

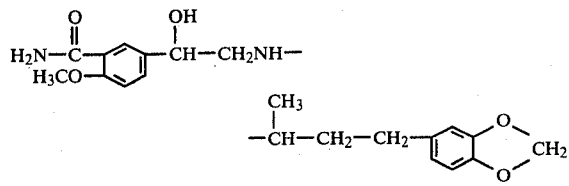

pharmaceutically acceptable salts and individual optical isomers thereof, pharmaceutical compositions comprising as the active ingredient the compound of Formula 1 or salts or isomers thereof and the use of said compound, or salt or isomer thereof or pharmaceutical composition comprising same in the treatment of hypertension.

4 Claims, No Drawings

NOVEL ANTIHYPERTENSIVE AGENT

FIELD OF INVENTION

This invention relates to a novel antihypertensive compound and composition and the use of same in the treatment of hypertension.

BACKGROUND OF INVENTION

The closest prior art known to applicants is contained in the following references:

Great Britain Pat. No. 1,260,521 to Allen & Hanburys Ltd. published Jan. 19, 1972.

U.S. Pat. No. 4,000,193 to Allen & Hanburys Ltd. published Dec. 28, 1976.

U.S. Pat. No. 3,644,353 to Allen & Hanburys Ltd. published Feb. 22, 1972.

U.S. Pat. No. 3,705,233 to Allen & Hanburys Ltd. published Dec. 5, 1972.

U.S. Pat. No. 3,732,300 to Allen & Hanburys Ltd. published May 8, 1973.

U.S. Pat. No. 4,012,444 to Allen & Hanburys Ltd. published Mar. 15, 1977.

U.S. Pat. No. 4,066,755 to Allen & Hanburys Ltd. published Jan. 3, 1978.

U.S. Pat. No. 3,883,560 to Richardson-Merrell Inc. published May 13, 1975.

Belgian Pat. No. 739,678 to Continental Pharm. published April 1, 1970.

None of these references discloses the specific compound of the present invention which is distinguishable over the prior art in view of the unexpected superior properties of said compound which are discussed in detail hereinafter.

SUMMARY OF INVENTION

The invention is to the compound 5-[2-[[3-(1,3-benzodioxol-5-yl)-1-methylpropyl]amino]-1-hydroxyethyl]-2-methoxybenzamide having the formula,

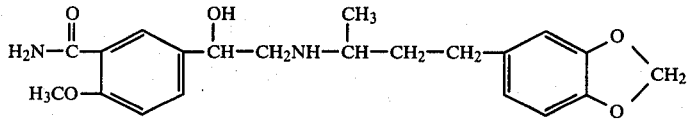

Formula I pharmaceutically acceptable salts and individual optical isomers thereof, pharmaceutical compositions comprising as the active ingredient the compound of Formula I or salts or isomers thereof and the use of said compound, or salt or isomer thereof or pharmaceutical composition comprising same in the treatment of hypertension.

Illustrative examples of pharmaceutically acceptable salts of the compound of this invention include non-toxic acid addition salts formed with inorganic acids, such as, hydrochloric, hydrobromic, sulfuric, and phosphoric acids; organic acids, for example, maleic, mandelic, salicyclic, benzoic or methanesulfonic. The salts of the compound of Formula I are prepared by procedures well known in the art.

In practicing the present invention the compound of Formula I as a salt or individual optical isomer thereof either alone or in combination with acceptable pharmaceutical carriers are administered to the patient to be treated either orally or parenterally, for example, subcutaneously or intravenously. As used herein the term patient is taken to mean a warm blooded animal, such as, mammals, including dogs, rats, cats and humans. The term hypertension includes primary or essential hypertension, hormonally induced hypertension and renal hypertension. A preferred mode of administration of the compound and salts thereof of the present invention is oral administration.

The compounds of Formula I and salts thereof may be formulated for oral administration as solid or liquid unit dosage forms. The solid dosage forms can be tablets, coated or uncoated; capsules, hard or soft; powders; granules; pills, enteric coated if desired. Solid diluents and carriers may be lactose, starch or other innocuous material with the usual tableting adjuncts as desired. Liquid oral compositions may be dispersions, suspensions, elixirs, syrups or simple solutions in aqueous vehicle. Polyethylene glycols including polyethylene glycol 300 have been found convenient oral vehicles. The term unit dosage form as used in the specification and claims means physically discrete units suitable as unitary administration for humans, each unit containing a predetermined quantity of active ingredient to achieve the desired therapeutic effect in association with the pharmaceutical carrier. Sterile, intraperitoneal formulation with physiologically acceptable vehicle, for example, saline, optionally buffered can also be utilized.

The amount of compound administered will vary over a wide range depending upon the patient to be treated and the severity of the hypertension and will be any antihypertensive effective amount of from about 1 mg/kg to 100 mg/kg of body weight of the patient per day. For example, a unit dosage form may suitably contain 250 mg of active ingredient as represented by Formula I or salt or isomer thereof which may be taken one or more times per day.

The compound of this invention was evaluated for α- and β-adrenergic receptor blocking activity as follows.

α-Adrenergic receptor blocking activity was determined in vitro by performing cumulative dose-response experiments in the isolated rabbit aortic strip preparation using norepinephrine as the agonist. The contractile response of the rabbit strip preparation in the presence of logarithmically increasing concentrations of the compounds being tested were expressed as percent of the maximal attainable response. Relative antagonistic potency was expressed as a $pA_2$ value. $pA_2$ is defined as the negative logarithm of the concentration of the antagonist which produces a doubling of the concentration of agonist required to produce a 50% maximal contraction.

β-Adrenergic receptor blocking activity was determined in vitro by performing cumulative dose-response experiments in the isolated guinea pig atria preparation using isoproterenol as the agonist. The response (increase in rate) of the guinea pig atria preparation in the presence of logarithmically increasing concentration of the compounds being tested were expressed as percent of the maximal attainable response. Relative antagonistic potency was expressed as a $pA_2$ value, as defined above.

The hydrochloride salt of the compound of Formula I (1) was found to give pA$_2$ values for α- and β-adrenergic receptor blocking activity of 5.14 and 8.46, respectively. The compound 5-[2-[[3-(1,3-benzodioxol-5-yl)-1-methylpropyl]amino]-1-hydroxyethyl]-2-hydroxybenzamide hydrochloride (2) described in U.S. Pat. No. 3,883,560 gave pA$_2$ values of 6.08 and 7.82, respectively. The known α-blocker phentolamine showed pA$_2$ of 7.78 and <5, respectively, and the known β-blocker propanolol showed pA$_2$ of <5 and 8.89, respectively. Thus, the ratio of β/α blocking activity for 1, 2, phentolamine and propranolol was >2089, 55, <0.002 and >7762, respectively.

Antihypertensive activity was determined in spontaneously hypertensive rats (SHR) of the Okomotor Aoki strain. Systolic blood pressure of the SHR was measured from the caudal artery by means of an indirect method utilizing a photocell transducer/tail cuff occluder system. Time response relationships were determined for each compound following an oral dose of 50 mg/kg. Data were expressed as mm Hg decrease from control values. Statistical significance was determined using a 2 tailed "t" test comparing drug treatment response values to those obtained from concurrent vehicle treated animals.

The hydrochloride salt of the compound of Formula I (1) was found to lower blood pressure by 42 and 67 mm Hg after 1 and 4 hours, respectively. The compound 5-[2-[[3-(1,3-benzodioxol-5-yl)-1-methylpropyl]amino]-1-hydroxyethyl]-2-hydroxybenzamide hydrochloride (2) described in U.S. Pat. No. 3,883,560 lowered blood pressure by 71 and 64 mm Hg after 1 and 4 hours, respectively. The known α-blocker phentolamine was found to lower blood pressure by 62 and 60 mm Hg, after 1 and 4 hours, respectively, while the known β-blocker propranolol did not lower blood pressure significantly after 1 and 4 hours, respectively.

These data indicate that the compound of this invention lowers blood pressure acutely by a direct action on blood vessels (vasodilation) and not by α-adrenergic blockage. This action, combined with the pronounced β-blocking activity gives the compound of this invention and its salts and isomers a unique pharmacologic profile and is superior to that of known prior art compounds, as well as that of the reference compounds phentolamine and propranolol. Since β-adrenergic receptor blockade is the cause of serious side effects, such as orthostatic hypertension and reflex tachycardia, in an agent used for therapy of hypertension (e.g., phentolamine) the absence of α-blocking activity in the compound (1) of this invention is advantageous while at the same time, its acute blood pressure lowering effect renders it superior to pure β-blockers, such as propranolol.

This α- and β-adrenergic receptor blocking activity can also be demonstrated in vivo using for example, anesthetized dogs, administering an appropriate agonist and measuring the antagonistic effect of the compound on cardiovascular responses.

The compound of Formula I is prepared by treating methyl 5-acetyl-2-methoxybenzoate or 5-acetyl-2-methoxybenzamide with a suitable brominating agent, such as bromine in an inert solvent, such as, tetrahydrofuran, chloroform or dioxane at a temperature of from 25° C. to reflux temperature. The thus obtained bromomethyl ketone derivative, that is, methyl 5-(2-bromoacetyl)-2-methoxybenzamide or 5-(2-bromoacetyl)-2-methoxybenzamide in an inert solvent, such as tetrahydrofuran, ether or dimethylformamide is added to a stirred solution of equivalent amounts of 3-(1,3-benzodioxol-5-yl)-1-methylpropylamine and a base, such as, a tri-(lower)alkylamine, for example, triethylamine at a temperature of about 0° to 50° C., preferably 25° C. The reaction time varies from about 1 to 24 hours and preferably is about 4 hours. Also, an excess of the reactant amine may be used supplanting the need to add a tri-(lower)alkylamine. The thus obtained benzodioxol derivative is reduced using catalytic hydrogenation employing a noble metal catalyst such as platinum or palladium on charcoal or a metal hydride reagent that is selective for reducing ketones in the presence of an ester function, such as, sodium borohydride. The reduction reaction is carried out in lower alcoholic solvents, such as, methanol or ethanol at temperatures varying from 0° to 25° C. to give methyl 5-[2-[[3-(1,3-benzodioxan-5-yl)-1-methylpropyl]amino]-1-hydroxyethyl]-2-methoxybenzoate when in the initial reaction methyl 5-acetyl-2-methoxybenzoate is employed or 5-[2-[[3-(1,3-benzodioxan-5-yl)-1-methylpropyl]amino]-1-hydroxyethyl]-2-methoxybenzamide when in the initial reaction 5-acetyl-2-methoxybenzamide is employed. The compound methyl 5-[2-[[3-(1,3-benzodioxan-5-yl)-1-methylpropyl]amino]-1-hydroxyethyl]-2-methoxybenzoate is then treated with ammonia in the presence of a catalyst such as sodium methoxide, sodium amide or dimethylaluminumamide in a lower alcoholic solvent, such as, methanol or ethanol. The reaction is carried out in an open or a closed vessel depending on the temperature of the reaction which may vary from about 25° to 100° C. The reaction is continued until thin layer chromatography (tlc) or spectral analysis of aliquots indicate the reaction is complete. The reaction time varies from about 1 to 10 days.

5-Acetyl-2-methoxybenzamide is prepared by treatment of methyl 5-acetyl-2-methoxybenzoate wherein the ketone is protected as the ketal by treatment with ethylene glycol with ammonia in the presence of a catalyst, such as, sodium methoxide, sodium amide or dimethylaluminumamide in a lower alcohol solvent, such as, methanol or ethanol. The reaction is carried out in an open or a closed vessel depending on the temperature of the reaction which may vary from about 25° to 100° C. with subsequent treatment with acid to regenerate the ketone.

The individual optical isomers can be separated by generally known procedures, for example, by using an optically active acid such as (−)-dibenzoyltartaric acid separating the diastereomeric acid salt and liberating the optical isomer as the base.

EXAMPLE 1

5-[2-[[3-(1,3-Benzodioxol-5-yl)-1-methylpropyl]amino]-1-hydroxyethyl]-2-methoxybenzamide hydrochloride A mixture of 66.1 g (0.341 mole) of methyl 5-acetyl-2-hydroxybenzoate, 7.26 g (0.511 mole) of methyl iodide and 47.0 g (0.341 mole) of potassium carbonate in 400 ml of sieve-dried dimethylformamide is stirred at room temperature for 65 hours. The mixture is poured on 1.5 liters of N hydrochloric acid, extracted 6 times with ethyl ether, washed extract with water, NaHCO$_3$ solution and cold 1 N NaOH, dried over Na$_2$SO$_4$, and evaporated solvent. Methyl 5-acetyl-2-methoxybenzoate, 51.3 g (72%) m.p. 95°–96° C., is obtained.

To a solution of 52.0 g (0.25 mole) of this ketone in 400 ml of chloroform is added a solution of 40.0 g (0.25 mole) of bromine in 200 ml of chloroform at such a rate as reaction mixture decolorizes (50 minutes after a 25 minute initiation period). Solvent is evaporated and the residue recrystallized from methanol to give 54.1 g (75%) of methyl 5-(2-bromoacetyl)-2-methoxybenzoate, m.p. 149°–153° C. A second crop of 10.4 g is obtained from the mother liquor.

A solution of 25.0 g (0.0871 mole) of this bromoketone in 850 ml of anhydrous tetrahydrofuran is added dropwise over 4 hours to a stirred solution of 16.8 g (0.0871 mole) of 3-(1,3-benzodioxol-5-yl)-1-methylpropylamine and 8.81 g (0.0871 mole) of triethylamine in 150 ml of tetrahydrofuran at 25° C. The mixture is stirred for another 3 hours. The resulting precipitate of triethylamine hydrobromide is removed by filtration and the filtrate is evaporated to dryness. The residue is dissolved in methanol (100 ml), 1 equivalent of methanolic HCl is added, and the solution is diluted with ethyl ether. The crude product (methyl 5-[2-[[3-(1,3-benzodioxol-5-yl)-1-methylpropyl]amino]acetyl]-2-methoxybenzoate hydrochloride) crystallizes in several portions, 15.9 g (46%) m.p. 185°–187° C. (dec.).

To a cold (ice-salt bath), solution of 15.9 g (0.0365 mole) of this ketone in 400 ml of methanol is added 6.90 g (0.182 mole) of sodium borohydride in portions over 45 minutes. The mixture is stirred for 30 minutes, then poured on ice-water, acidified with 20% acetic acid (500 ml), made basic with NaHCO$_3$ and extracted with methylene chloride. The extract is washed with water and dried over MgSO$_4$ and the solvent is evaporated to give crude methyl 5-[2-[[3-(1,3-benzodioxan-5-yl)-1-methylpropyl]amino]-1-hydroxyethyl]-2-methoxybenzoate (12.1 g). A sample of the hydrochloride salt has m.p. 159°–162° C.; elemental analysis and spectra agree with the assigned structure.

The ester (free base, 6.8 g) is dissolved in methanol to which a small piece (about 100 mg) of sodium had been added (to form sodium methoxide), the solution is cooled (0° C.) and saturated with gaseous ammonia. The resulting mixture is stirred at room temperature for several days. The reaction is followed by thin layer chromatography. When all ester has been converted to amide, solvent is evaporated. The residue is taken up in ethyl acetate, the solution is washed with NaHCO$_3$ solution, dried over MgSO$_4$, and evaporated to dryness. The residue is dissolved in methanol, 1 equivalent of methanolic HCl is added and the compound 5-[2-[[3-(1,3-benzodioxol-5-yl)-1-methylpropyl]amino]-1-hydroxyethyl]-2-methoxybenzamide hydrochloride crystallizes after addition of ethyl ether, 2.5 g, m.p. 147°–156° C. (dec.). Elemental analysis and spectra agree with the assigned structure.

I claim:

1. A compound of the formula

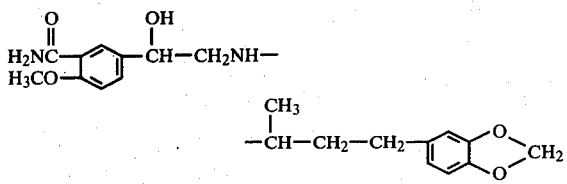

or a pharmaceutically acceptable acid addition salt or individual optical isomer thereof.

2. A compound of claim 1 which is 5-[2-[[3-(1,3-benzodioxol-5-yl)-1-methylpropyl]amino]-1-hydroxyethyl]-2-methoxybenzamide hydrochloride.

3. A pharmaceutical composition in unit dosage form comprising an effective amount of a compound of claim 1 and a significant amount of a pharmaceutically acceptable carrier.

4. A method of treating hypertension in a patient in need thereof which comprises administering to said patient an antihypertensive effective amount of a compound of claim 1.

* * * * *